(12) United States Patent
Thomas (10) Patent No.: US 8,627,972 B2
(45) Date of Patent: Jan. 14, 2014

(54) LOWER CONTAINER PART AND UPPER CONTAINER PART OF A STERILE CONTAINER AND STERILE CONTAINER

(75) Inventor: Stefan Thomas, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 146 days.

(21) Appl. No.: 13/135,596

(22) Filed: Jul. 7, 2011

(65) Prior Publication Data

US 2012/0012580 A1   Jan. 19, 2012

(30) Foreign Application Priority Data

Jul. 19, 2010   (DE) .......................... 10 2010 036 489

(51) Int. Cl.
*B65D 6/28* (2006.01)
*B65D 45/16* (2006.01)
*B65D 53/00* (2006.01)
*A61B 19/02* (2006.01)

(52) U.S. Cl.
USPC .......... 220/4.21; 220/324; 220/378; 206/349; 206/363; 206/438; 206/828

(58) Field of Classification Search
USPC ......... 220/4.21, 319, 320, 324, 378; 206/339, 206/349, 363, 438, 828
See application file for complete search history.

(56) References Cited

U.S. PATENT DOCUMENTS

| | | | |
|---|---|---|---|
| 4,512,498 A | | 4/1985 | Leibinger |
| 4,919,888 A | * | 4/1990 | Spence ............................ 422/26 |
| 5,641,065 A | * | 6/1997 | Owens et al. .................. 206/370 |
| 6,371,326 B1 | * | 4/2002 | Gabele et al. .................. 220/326 |
| 7,914,751 B2 | * | 3/2011 | Oertmann ....................... 422/297 |
| 2002/0079286 A1 | | 6/2002 | Haynes et al. |
| 2004/0159236 A1 | | 8/2004 | Otsuka et al. |
| 2006/0151509 A1 | * | 7/2006 | Eiskant et al. ................. 220/782 |

FOREIGN PATENT DOCUMENTS

| | | |
|---|---|---|
| DE | 1 908 434 | 1/1965 |
| DE | 35 00 026 | 7/1986 |
| EP | 1 405 799 | 4/2004 |

OTHER PUBLICATIONS

BAL SEAL Engineering brochure showing a spring sealing for EMC shielding, (date unknown, downloaded Jun. 29, 2011) four pages.

* cited by examiner

*Primary Examiner* — Anthony Stashick
*Assistant Examiner* — Madison L Poos
(74) *Attorney, Agent, or Firm* — Lipsitz & McAllister, LLC (57) ABSTRACT

A sterile container having a lower container part and an upper container part for closing the lower container part is provided. The lower and upper container parts define, in a closed position, a container interior. A sealing device is provided for gastight sealing of the sterile container in the closed position. The sealing device comprises a circumferential sealing element bearing against both the lower and upper container parts in the closed position. The sealing element comprises an upper container part sealing section with an upper container part sealing surface region bearing against the upper container part, and a lower container part sealing section with a lower container part sealing surface region bearing against the lower container part. The sealing device further comprises a pretensioning device for exerting a pretensioning force on at least the lower container part sealing section or on the upper container part sealing section.

25 Claims, 5 Drawing Sheets

LOWER CONTAINER PART AND UPPER CONTAINER PART OF A STERILE CONTAINER AND STERILE CONTAINER

This application claims the benefit of German Patent Application No. 10 2010 036 489.4 filed on Jul. 19, 2010.

The present disclosure relates to the subject matter disclosed in German application number 10 2010 036 489.4 of Jul. 19, 2010, which is incorporated herein by reference in its entirety and for all purposes.

FIELD OF THE INVENTION

The present invention relates to sterile containers generally.

The present invention more specifically relates to a lower container part of a sterile container, the lower container part being closable by an upper container part of the sterile container.

The present invention more specifically further relates to an upper container part of a sterile container, the upper container part being designed to close a lower container part of the sterile container.

The present invention more specifically also relates to a sterile container having a lower container part and an upper container part for closing the lower container part, the lower container part and the upper container part defining, in a closed position, a container interior.

BACKGROUND OF THE INVENTION

Sterile containers, also referred to as sterilization containers, with lower container parts and upper container parts of the kind described at the outset are known in manifold forms. They serve in a known manner, in particular, for germ-free storage of previously cleaned and sterilized surgical instruments and implants. Sealing cords, sealing lips and similar sealing elements made of silicone, silicone foams and similar materials are mainly used as sealing elements. The partly only poor compression variability of these known sealing elements, which ensures sealing in only a small, defined distance range of the geometries of lower container part and upper container part that are to be sealed off relative to one another, is problematic.

Sterile containers that are in permanent use age. Firstly, the sealing element itself is subject to aging processes. In particular, it may wear and partly or completely lose its elasticity. Furthermore, troughs defining lower container parts or lids of the sterile containers defining upper container parts may become warped or bent as a result of knocks and blows. The originally defined distances in the region of the sealing element between upper container part and lower container part are thereby changed. Depending on the sealing element used, leakages may then occur on the container, as a result of which germ-proof sealing of the sterile container is no longer ensured.

Furthermore, the aging of rubber-elastic sealing materials leads to a time limit for use of such known sealing elements, and, consequently, after the sterile container has been in operation for several years, it is not possible to assess the state of the sealing element with certainty or only with great difficulty.

Therefore, it would be desirable to provide a lower container part, an upper container part and a sterile container which ensure a permanent germ-proof sealing of the sterile container in the closed position.

SUMMARY OF THE INVENTION

In a first aspect of the invention, a lower container part of a sterile container is provided, said lower container part is closable by an upper container part of the sterile container. Said lower container part and said upper container part define, in a closed position, a container interior. A sealing device is held on said lower container part for the gastight or germ-proof sealing of the sterile container in the closed position. Said sealing device comprises a circumferential sealing element bearing against the lower container part and adapted to be placed against the upper container part. Said sealing element comprises a lower container part sealing section with a lower container part sealing surface region bearing against the lower container part, and an upper container part sealing section with an upper container part sealing surface region adapted to be placed against the upper container part. And said sealing device comprises a pretensioning device for exerting a pretensioning force on at least the upper container part sealing section in the direction away from the lower container part In a second aspect of the invention, an upper container part of a sterile container is provided. Said upper container part is designed to close a lower container part of the sterile container. Said upper container part and said lower container part define, in a closed position, a container interior. A sealing device is held on said upper container part for the gastight or germ-proof sealing of the sterile container in the closed position. Said sealing device comprises a circumferential sealing element bearing against the upper container part and adapted to be placed against the lower container part. Said sealing element comprises an upper container part sealing section with an upper container part sealing surface region bearing against the upper container part, and a lower container part sealing section with a lower container part sealing surface region adapted to be placed against the lower container part. And said sealing device comprises a pretensioning device for exerting a pretensioning force on at least the lower container part sealing section in the direction away from the upper container part.

In a third aspect of the invention, a sterile container has a lower container part and an upper container part for closing the lower container part. Said lower container part and said upper container part define, in a closed position, a container interior. A sealing device is provided for the gastight or germ-proof sealing of the sterile container in the closed position. Said sealing device comprises a circumferential sealing element bearing against both the lower container part and the upper container part in the closed position. Said sealing element comprises an upper container part sealing section with an upper container part sealing surface region bearing against the upper container part, and a lower container part sealing section with a lower container part sealing surface region bearing against the lower container part. And said sealing device comprises a pretensioning device for exerting a pretensioning force on at least the lower container part sealing section in the direction towards the lower container part or on the upper container part sealing section in the direction towards the upper container part.

BRIEF DESCRIPTION OF THE DRAWINGS

The foregoing summary and the following description may be better understood in conjunction with the drawing figures, of which.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a lower container part of a sterile container, said lower container part being closable by an upper container part of the sterile container, said lower container part and said upper container part defining, in a closed position, a container interior, a sealing device being held on said lower container part for the gastight or germ-proof sealing of the sterile container in the closed position, said sealing device comprising a circumferential sealing element bearing against the lower container part and adapted to be placed against the upper container part, said sealing element comprising a lower container part sealing section with a lower container part sealing surface region bearing against the lower container part, and an upper container part sealing section with an upper container part sealing surface region adapted to be placed against the upper container part, and said sealing device comprising a pretensioning device for exerting a pretensioning force on at least the upper container part sealing section in the direction away from the lower container part.

Provision of such a pretensioning device ensures, in particular, that the sealing element is pressed in a defined manner against both the lower container part and the upper container part in the closed position. When the sealing element ages and increasingly loses its originally elastic properties, this has practically no effect on a lower container part as proposed above, as the pretensioning device essentially defines the elasticity of the sealing device in the long term. The sealing element itself then only requires a low compression variability as this is assumed by the pretensioning device. In this way, a significantly longer service life of sterile containers is achievable than is the case with conventional sterile containers. In the case of the proposed lower container part, the classic sealing function of the sealing device is essentially separated into two functions performed, on the one hand, by the pretensioning device and, on the other hand, by the sealing element. The pretensioning device has predominantly a spring effect, and the tightness can be achieved by the sealing element. Compressibility and tightness properties of the sealing device can thus be specifically optimized by appropriate choice of pretensioning device and sealing element, since, in particular, sealing devices made of two different materials are possible.

The present invention further relates to an upper container part of a sterile container, said upper container part being designed to close a lower container part of the sterile container, said upper container part and said lower container part defining, in a closed position, a container interior, a sealing device being held on said upper container part for the gastight or germ-proof sealing of the sterile container in the closed position, said sealing device comprising a circumferential sealing element bearing against the upper container part and adapted to be placed against the lower container part, said sealing element comprising an upper container part sealing section with an upper container part sealing surface region bearing against the upper container part, and a lower container part sealing section with a lower container part sealing surface region adapted to be placed against the lower container part, and said sealing device comprising a pretensioning device for exerting a pretensioning force on at least the lower container part sealing section in the direction away from the upper container part.

Such an upper container part offers in an analogous manner the advantages described above in conjunction with the lower container part.

The present invention further relates to a sterile container having a lower container part and an upper container part for closing the lower container part, said lower container part and said upper container part defining, in a closed position, a container interior, a sealing device being provided for the gastight or germ-proof sealing of the sterile container in the closed position, said sealing device comprising a circumferential sealing element bearing against both the lower container part and the upper container part in the closed position, said sealing element comprising an upper container part sealing section with an upper container part sealing surface region bearing against the upper container part, and a lower container part sealing section with a lower container part sealing surface region bearing against the lower container part, and said sealing device comprising a pretensioning device for exerting a pretensioning force on at least the lower container part sealing section in the direction towards the lower container part or on the upper container part sealing section in the direction towards the upper container part.

As explained above in conjunction with the first aspect of the invention, characteristics of the sealing device can be improved by separating the functions pretensioning/elasticity/compressibility and sealing. With a pretensioning device which exhibits practically no aging, the sealing device may, all in all, have a very long service life even if the sealing element itself increasingly loses its elastic properties in the course of time. All in all, sterile containers can thus be created, which in comparison with conventional sterile containers have significantly longer service lives, as the improved sealing device has a significantly longer life span than conventional seals, for example, silicone profiles.

All additional features described below can be provided in connection with at least one of the lower container part, the upper container part and the sterile container described above.

A particularly secure sealing between lower container part and upper container part in the closed position can be achieved, in particular, by the pretensioning device being arranged so as to exert a pretensioning force on the lower container part sealing section and on the upper container part sealing section. This allows the sealing element to be pressed with a single pretensioning device against the lower container part and the upper container part in such a way that the container interior can be permanently closed in a germ-proof manner.

The germ-proofness in the closed position of a sterile container can be further improved by the lower container part sealing section and the lower container part being arranged for movement relative to each other, and/or by the upper container part sealing section and the upper container part being arranged for movement relative to each other. In this way, any deformations arising from damage on the lower container part or on the upper container part can be compensated for by the sealing device without there being any risk of the required germ-proofness of the sterile container no longer being ensured.

In order to prevent the sealing device from becoming detached from the sterile container or a part thereof in an undesirable manner, it is advantageous for the lower container part sealing section to be firmly connected to the lower container part or for the upper container part sealing section to be firmly connected to the upper container part. In other words, the sealing device can, for example, be fixed to the lower container part or to the upper container part, and then interact with the respective other part when the sterile container is closed so as to seal the container interior.

The sealing device may, in principle, be configured so as to be detachably connectable to the lower container part or to the upper container part. To permanently prevent the sealing device from being detachable from the lower container part or from the upper container part of the sterile container, it is expedient for the lower container part sealing section to be undetachably connected to the lower container part or for the upper container part sealing section to be undetachably connected to the upper container part.

Particularly good sealing can be achieved, in particular, by the sealing element being of integral configuration. With a circumferential sealing surface on the lower container part and on the upper container part there are, therefore, no additional gaps between a beginning and an end of the sealing element.

It is advantageous for the sealing element to be of tube-shaped or pipe-shaped configuration. This makes it possible, in particular, to arrange the pretensioning device in an interior defined by the sealing element, whereby the sealing element forms, so to speak, a sheath for the pretensioning device and, for example, can also protect it against aging or corrosion.

The sealing element preferably defines a circumferential cavity. On the one hand, this may serve to receive the pretensioning device. On the other hand, it may also be part of an additional sealing lip which bears against the upper container part or against the lower container part.

In order to ensure in a simple way that the pretensioning device can have a pretensioning effect on the sealing element, in particular, on parts thereof, it is advantageous for the pretensioning device to be at least partly covered or surrounded by the sealing element. In particular, the pretensioning device can be arranged in such a way that the upper container part sealing section and the lower container part sealing section are pressed in the closed position against contact surfaces provided therefor on the upper container part and the lower container part.

Particularly good protection of the pretensioning device can be achieved, in particular, by the sealing element completely enclosing the pretensioning device.

The structure of the pretensioning device is particularly simple if it comprises at least one pretensioning member which exerts a pretensioning force on at least the lower container part sealing section in the direction towards the lower container part or on the upper container part sealing section in the direction towards the upper container part. The at least one pretensioning member thus serves to press partial areas of the sealing element that are provided for sealing upper container part and lower container part against the upper container part or the lower container part.

In principle, it is possible to provide two or more pretensioning members, which then jointly form the pretensioning device. The construction and the manufacture of the sterile container and also of the parts forming it can be further simplified by only a single pretensioning member of self-contained configuration being provided. This can, for example, be easily pushed into a recess provided for it in the sealing element.

In accordance with a further preferred embodiment of the invention, it may be provided that the at least one pretensioning member defines a pretensioning member longitudinal line, and that the at least one pretensioning member bears with an outer surface, oriented transversely, in particular, perpendicularly, to the pretensioning member longitudinal line, against the upper container part sealing section and/or against the lower container part sealing section. Therefore, what is special about this configuration is that the at least one pretensioning member does not act in the direction of its pretensioning member longitudinal line, for example, a helical axis or helical line in a spiral spring, but precisely in a direction transverse to this pretensioning member longitudinal line. This does, however, have the advantage that an elastic deformation of the pretensioning member results in practically no change in the length thereof in the direction of the pretensioning member longitudinal line. An elasticity of the at least one pretensioning member can thus be set, in particular, by the choice and strength of the material used to form the at least one pretensioning member.

It may also be expedient for the at least one pretensioning member to define a pretensioning member longitudinal line, and for the at least one pretensioning member to exert a force acting transversely, in particular, perpendicularly, to the pretensioning member longitudinal line on the upper container part sealing section and/or the lower container part sealing section. What is special about this configuration is, therefore, that the at least one pretensioning member does not act in the direction of its pretensioning member longitudinal line, for example, a helical axis or helical line in a spiral spring, but precisely in a direction transverse to this pretensioning member longitudinal line.

A particularly simple structure of the sealing device can be achieved, in particular, by the at least one pretensioning member comprising a helical spring or being configured in the form of a helical spring. Helical springs are simple to manufacture, in particular, also with spring constants that can be set in a precisely defined manner, for example, by appropriate selection of the material and in dependence upon a strength of the material from which the helical spring is wound. The helical spring is preferably wound obliquely in relation to a helical line defined by it, so that individual windings of the helical spring do not extend essentially in a plane perpendicular to the helical line, but are already inclined at an angle of inclination relative thereto, for example, through 45° in a normal position of the helical spring in which no outer forces are acting thereon. In this case, one can also say that the windings defining the helical spring lie tilted to the helical line or helical axis.

Damage to the sealing element by the at least one pretensioning member can be eliminated in a simple way, in particular, by the helical spring being of self-contained configuration. If it is bent out of a wire material of circular or oval cross section, it then has no beginning and no end and, therefore, no sharp corners or edges either.

In accordance with a further preferred embodiment of the invention, it may be provided that the helical spring defines an all-round helical line, and that the helical spring exerts a force acting transversely, in particular, perpendicularly, to the pretensioning member longitudinal line on the upper container part sealing section and/or on the lower container part sealing section. The helical spring does therefore not exert a force on the sealing element along its pretensioning member longitudinal line, which is typically the case for compression or tension springs, but instead perpendicularly to the helical line. The helical line forms that line around which the windings of the helical spring extend. As a rule, it therefore extends entirely within the helical spring.

The manufacture of the sealing element can be further simplified by it being configured in the form of a profiled strand. For example, it can thus be produced by injection molding or extrusion from a suitable plastic material, for example, an elastomer or a plastic material with at least partly elastomeric properties.

The sealing element preferably comprises a pretensioning device receptacle for at least partly receiving the pretensioning device. To prepare or assemble the sealing device, the pretensioning device can then be fully or partly inserted into the pretensioning device receptacle.

It is advantageous for the pretensioning device receptacle to be open circumferentially. This allows the sealing element to be of integral and self-contained configuration and a pretensioning member, which is also of integral and self-contained configuration, to be laterally inserted into the pretensioning device receptacle. In this way, seamlessly configured sealing elements and pretensioning members can be easily and securely connected to one another.

Alternatively, it may also be advantageous for the pretensioning device receptacle to be closed. This makes it possible to arrange the pretensioning member or the pretensioning device completely in the interior, defining, for example, a circumferential cavity, of the sealing element in the pretensioning device receptacle, so that the sealing element can protect the pretensioning device against aging or corrosion, for example.

It is expedient for the sealing device to be arranged in a circumferential groove on the upper container part or on the lower container part. The sealing device can thus be securely fixed in a simple way. A projection, for example, which engages the groove and presses against the sealing device in the closed position can be formed on the respective other container part.

In order to minimize the risk of the pretensioning device becoming detached in an undesirable manner from the lower container part, from the upper container part or from the sterile container, it is expedient for the pretensioning device to be held on the sealing element. If the sealing element is held securely on the sterile container or on a part thereof, the pretensioning device is then also automatically held and positioned in a desired manner.

In order to prolong the service life of the sterile container and the parts forming it, it is advantageous for the pretensioning device to be at least partly made of a metal. In particular, permanently and specifically desired pretensioning forces which are to be exerted by the pretensioning device can thus be defined and conserved.

Metals containing copper and/or beryllium are particularly well suited. Desired spring constants can be optimally implemented with these.

The manufacture of the sealing device is simplified and the costs thereof minimized if the sealing element is made of a plastic material.

Particularly good sealing results are obtained when the plastic material contains rubber and/or polytetrafluoroethylene.

Figure 1:
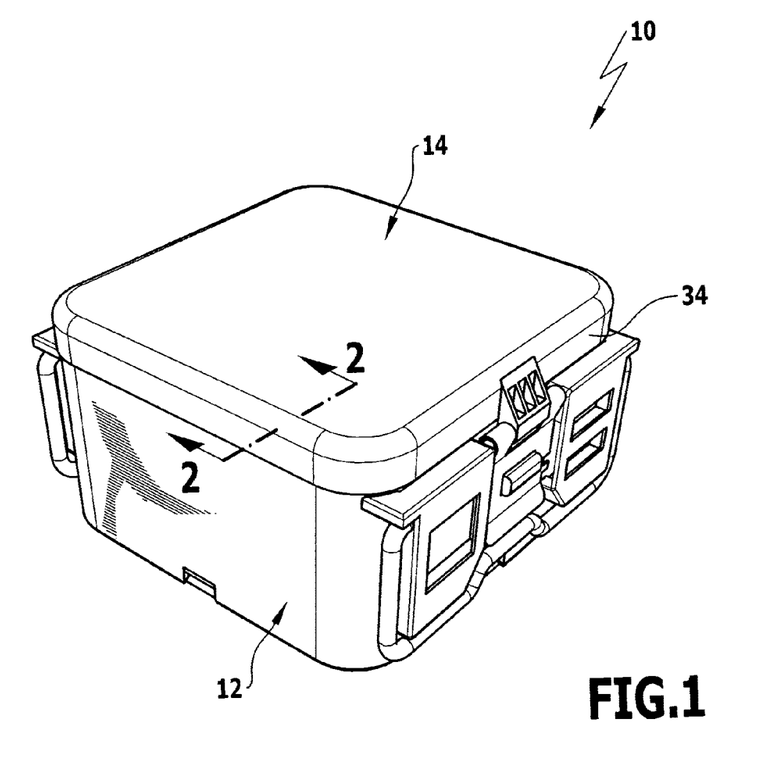
FIG. 1 shows a diagrammatic perspective view of a first embodiment of a sterile container with a lower container part and an upper container part.

A sterile container, also referred to as sterilization container, generally designated by reference numeral 10, is represented diagrammatically in FIG. 1. It comprises a lower container part 12 in the form of a trough and an upper container part 14 in the form of a lid for closing the lower container part 12. In a closed position of the sterile container 10 shown in FIG. 1, walls of the lower container part 12 and of the upper container part 14 delimit a container interior 16.

A sealing device 18 serves to seal the container interior 16 in the closed position. It comprises a circumferential sealing element 20, which is arranged on the lower container part 12 or alternatively on the upper container part 14, as shown diagrammatically in FIGS. 2 and 3, in a circumferential groove 22 on the upper container part 14. Alternatively, a corresponding groove for receiving the sealing device 18 could also be provided on the lower container part 12.

Figure 2:
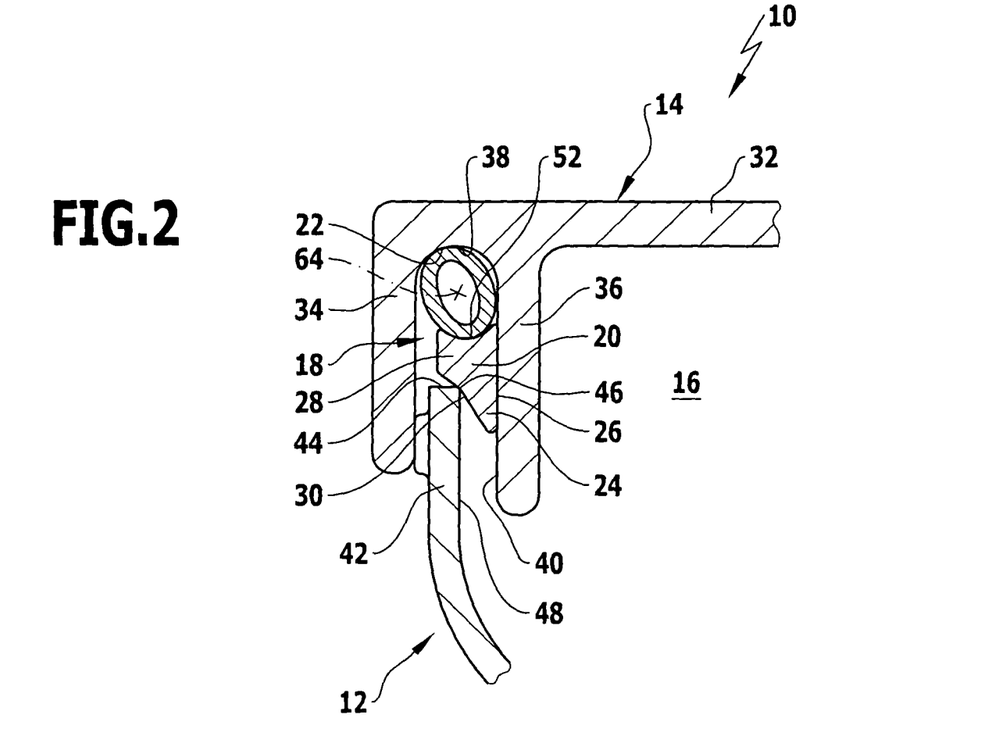
FIG. 2 shows a sectional view taken along line 2-2 in FIG. 1 in the closed, germ-proof sterile container.
Figure 3:
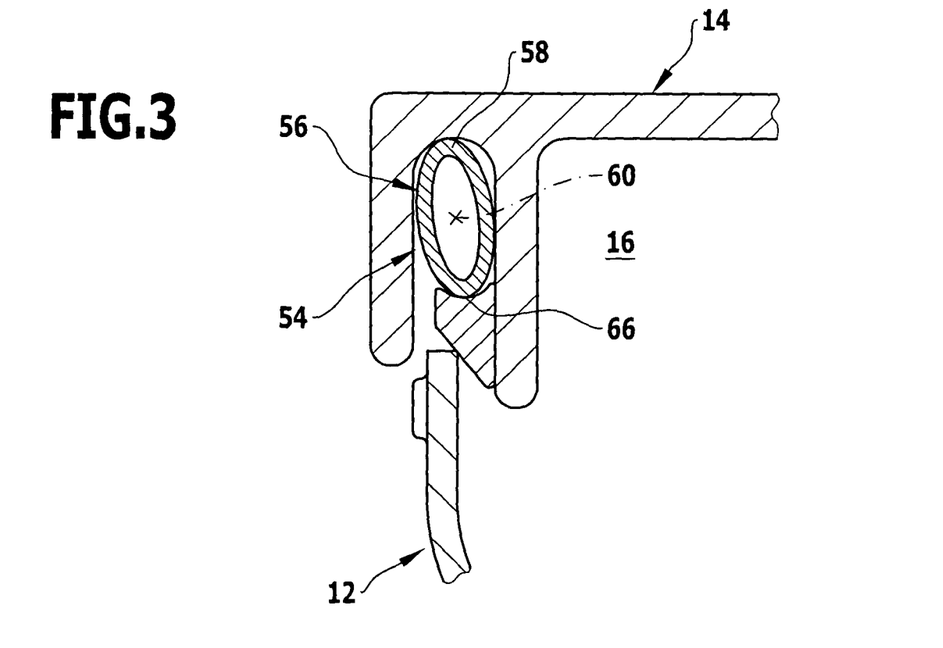
FIG. 3 shows a sectional view taken along line 2-2 when removing the upper container part from the lower container part.

The sealing element 20 comprises an upper container part sealing section 24 with an upper container part sealing surface region 26 bearing against the upper container part 14. Furthermore, the sealing element 20 comprises a lower container part sealing section 28 with a lower container part sealing surface region 30 bearing against the lower container part 12.

The groove 22 is defined by two side walls 34 and 36 extending parallel to each other and perpendicularly from a lid wall 32. The side wall 34 delimits the upper container part 14 laterally outwards and is slightly shorter than the side wall 36 spaced somewhat from it. A groove bottom 38 is semicircular in cross section and is concavely curved in the direction facing the lower container part 12.

The upper container part sealing surface region 26 is of flat configuration and bears with surface-to-surface contact against a wall surface 40 of the side wall 36 that faces in the direction of the side wall 34. An end section 42 of the lower container part 12 that faces in the direction of the upper container part 14 is configured in the form of a wall and has a flat end face 44 facing in the direction of the groove bottom 38. A circumferential longitudinal edge 46, which is defined between the end face 44 and an inner surface 48 of the end section 42 that faces the wall surface 40, bears against the slightly concavely curved lower container part sealing surface region 30 facing in the direction of the lower container part 12.

Facing away from the direction of the groove bottom 38, the sealing element 20 has a contact surface 30 which, in a normal position, as shown diagrammatically in FIG. 3, is flat, and, in a closed position, as shown diagrammatically in FIG. 2, is slightly convexly curved.

Figure 6:
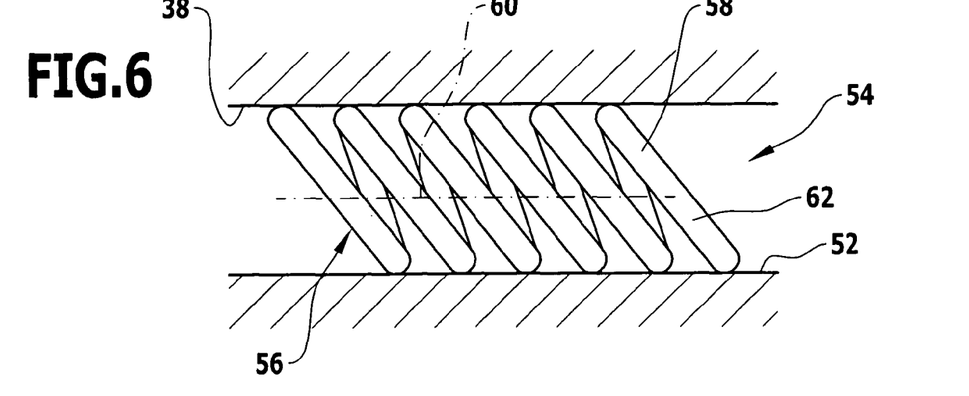
FIG. 6 shows a diagrammatic representation of the pretensioning device in a normal position.

The sealing device 18 further comprises a pretensioning device 54 having a pretensioning member 56 in the form of a self-contained helical spring 58 held in the groove 22. The pretensioning member 56 is supported, on the one hand, substantially on the groove bottom 38 and, on the other hand, on the contact surface 52. The helical spring 58 is wound obliquely in relation to a helical line 60 defined by it, so that single windings 62 of the helical spring 58 do not extend essentially in a plane perpendicular to the helical line 60, but are already inclined at approximately 45° relative to the latter in a normal position of the helical spring 58 in which no outer forces are acting on it. This is shown diagrammatically in FIG. 6.

The pretensioning member 56 defines a pretensioning member longitudinal line 64, which corresponds to the helical line 60. The pretensioning member 56 thus exerts a force acting transversely, in particular, perpendicularly to the pretensioning member longitudinal line 64 on the upper container part sealing section 24 and on the lower container part sealing section 28. One could also say that the pretensioning member 56 bears indirectly against the upper container part sealing section 24 and against the lower container part sealing section 28 via the contact surface 52 with an outer surface 66 oriented transversely, in, particular, perpendicularly, to the pretensioning member longitudinal line 64.

The helical spring 58 is of integral and self-contained configuration, so that only a single pretensioning member 56 is provided. It is conceivable to also provide two or more pretensioning members 56 in the form of helical springs 58 whose free ends are connected to each other.

The pretensioning device 54 shown diagrammatically in FIGS. 2 and 3 is partly covered or surrounded by the sealing element 20. In the variant of a sealing device 18 shown diagrammatically in FIGS. 2 and 3, the upper container part sealing section 24 is firmly, but movably connected to the upper container part 14. Alternatively, the arrangement could also be configured conversely by the lower container part sealing section being firmly, but movably connected to the lower container part 12.

Furthermore, it is also conceivable to undetachably connect the lower container part sealing section 28 to the lower container part 12. Alternatively, the upper container part sealing section 24 may also be undetachably connected to the upper container part 14. All in all, the pretensioning device 54 is thus arranged for exerting a pretensioning force on the lower container part sealing section 28 and the upper container part sealing section 24.

The lower container part sealing section 28 and the lower container part 12 are arranged for movement relative to each other. In particular, the lower container part 12 may be completely detached from the lower container part sealing section 28. The upper container part sealing section 24 is also arranged for movement relative to the upper container part 14.

Figure 7:
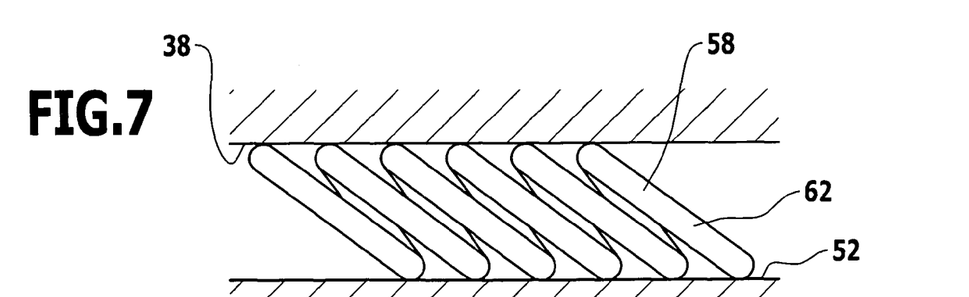
FIG. 7 shows a view in analogy with FIG. 6 with a partly pretensioned pretensioning member.
Figure 8:
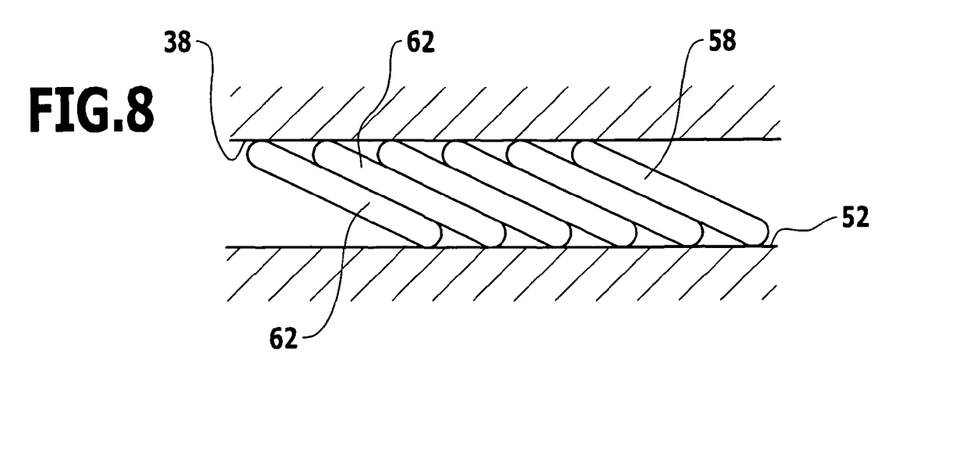
FIG. 8 shows a view in analogy with FIG. 6 with the pretensioning member pretensioned at its maximum.

When the upper container part 14, as shown diagrammatically in FIG. 3, is placed on the lower container part 112, the longitudinal edge 46 and the lower container part sealing surface region 30 first enter into contact with each other. When the upper container part 14 is pushed further in the direction towards the lower container part 12, the helical spring 58 is pretensioned perpendicularly to its helical line 60. This results in the windings 62 becoming further inclined relative to the helical line 60, as shown diagrammatically in FIG. 7, and, in FIG. 8, as the pressure on the helical spring 58 progresses further. A maximum inclination of the windings 62 is reached when these, as shown diagrammatically in FIG. 8, lie with surface-to-surface contact against one another.

Figure 4:
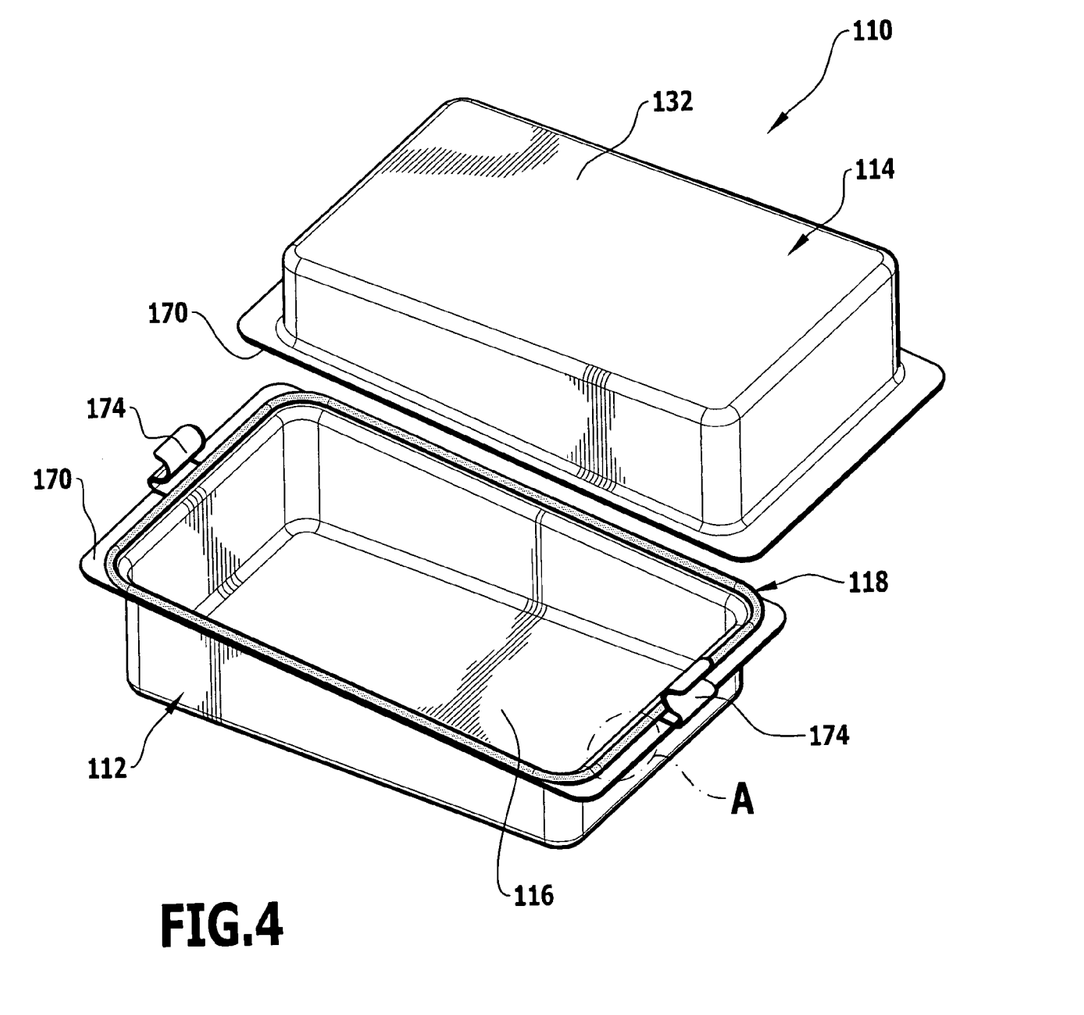
FIG. 4 shows a diagrammatic perspective general view of an alternative embodiment of a sterile container.

An alternative embodiment of a sterile container, generally designated by reference numeral 110, is shown diagrammatically in FIG. 4. It comprises a lower container part 112 in the form of a trough and an upper container part 114 of essentially identical construction for closing the lower container part 112. They again define a container interior 116 in a closed position. A sealing surface 170 of the lower container part 112 and a sealing surface 170 of the upper container part 114 define a plane which is inclined somewhat relative to a plane defined by the lid wall 132.

Figure 5:
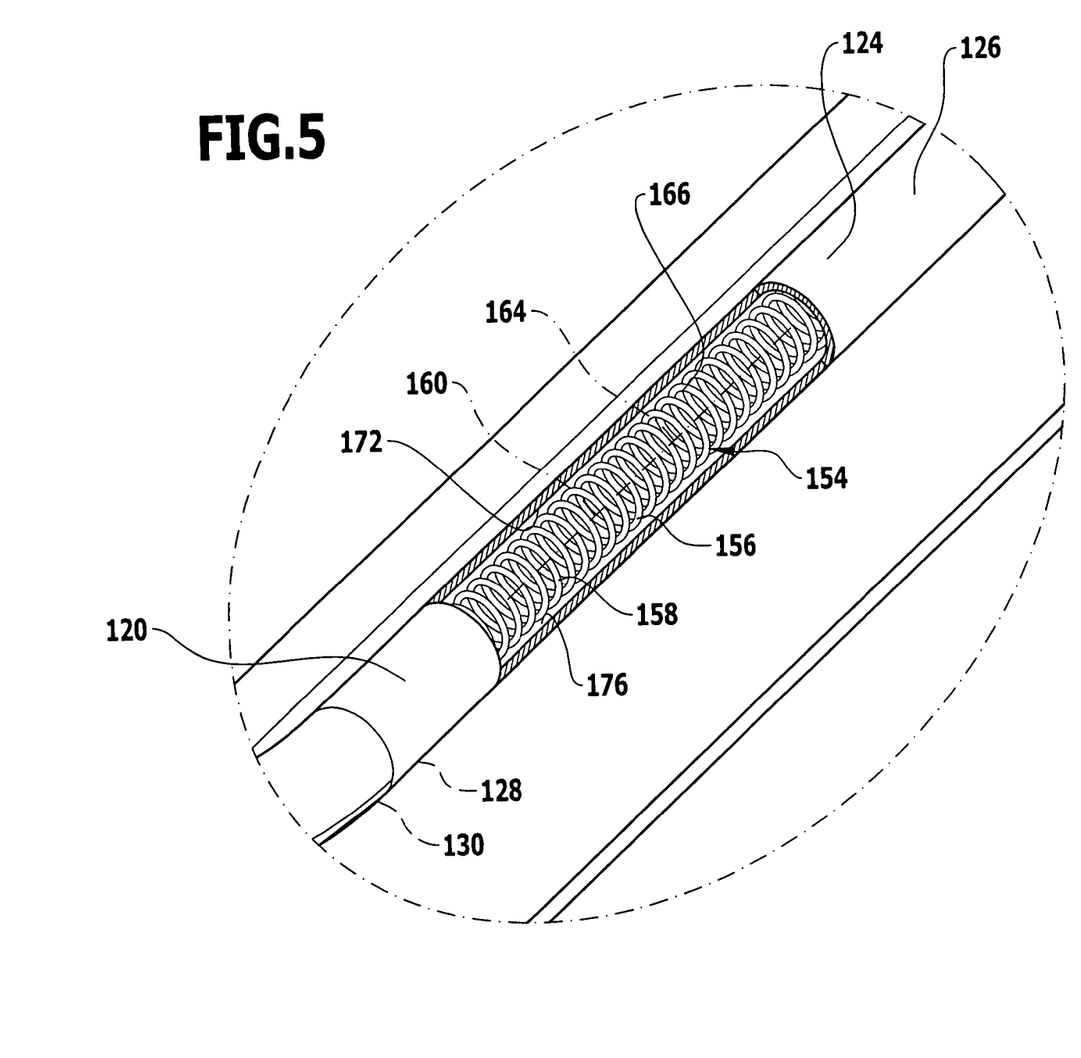
FIG. 5 shows an enlarged and partly broken-open view of region A in FIG. 4.

A sealing device 118 is held on the sealing surface 170 of the lower container part 112. It comprises a self-contained, tube-shaped sealing element 120, which defines a circumferential, hollow pretensioning device receptacle 172 defining a cavity 176 in which there is held a pretensioning device 154 comprising a pretensioning member 156, defining a pretensioning member longitudinal line 164, in the form of a helical spring 158 defining a helical line 160. The sealing element 120 thus completely encloses the pretensioning device 154. Alternatively, it is also conceivable to construct the sealing element 120 in the form of a profiled strand similar to the sealing element 120, with the profiled strand basically having the shape of a tube, but comprising a circumferential, lateral opening towards the pretensioning device receptacle 172, through which opening the pretensioning member 156 can be inserted into the cavity 176.

The sealing element 120 may, for example, be adhesively bonded or welded to the sealing surface 170. It is thus firmly connected to the lower container part 112 and holds the pretensioning device 154 in position in a defined manner. Alternatively, it is also possible to arrange and secure the sealing device 118 in an analogous manner on the upper container part 114.

For germ-proof closure of the sterile container 110, the upper container part 114 is placed with its sealing surface 170 on the sealing element 120. An upper container part sealing section 124, which defines an upper container part sealing surface region 126, is thereby pressed against an outer surface 166 of the helical spring 158. In an analogous manner, the outer surface 166 is also pressed against a lower container part sealing section 128, which defines a lower container part sealing surface region 130.

Clip-shaped closure elements 174 arranged at end faces of the lower container part 112 enable the upper container part 114 with a partly deflected pretensioning device 154 to be held in the closed position. The deformation of the helical spring 158 upon closing the sterile container 110 takes place in analogy with the deformation of the helical spring 58 shown in FIGS. 6 to 8. The helical spring 158 ensures that the upper container part sealing surface region 126 and the lower container part sealing surface region 130 lie permanently and securely against the sealing surfaces 170 of the lower container part 112 and the upper container part 114.

The helical springs 58 and 158 are preferably made of a metal, and, in particular, alloys of copper and beryllium are particularly well suited. The sealing elements 20 and 120 are made of a plastic material, for example, by injection molding or extrusion. Owing to the provision of the pretensioning device 54 or 154, there is no necessity for the plastic material, in particular, also in the long term, to possess great elastic properties, so that, in particular, also polytetrafluorethylene is suitable as material for producing the sealing elements 20 and 120. Optionally, the sealing elements 20 and 120 may also be made of an elastomer or contain one, for example, rubber.

Further alternative sterile container designs with corresponding sealing devices comprising pretensioning devices are, of course, conceivable. The special characteristics, in particular, of the sealing elements 20 and 120, are essentially achieved by a pretensioning effect of the pretensioning members 56 and 156 occurring transversely to a pretensioning member longitudinal line 64 or 164 defined by these, and not, as is usually the case with helical springs, parallel to the helical lines defined by these.

The required pretensioning forces can be set in a specific manner by the design of the pretensioning members 56 and 156, in particular, by the selection of suitable materials and appropriate dimensions, for example, of a diameter of the helical springs 58 and 158 and of the wire material used for the winding of these.

The invention claimed is:

1. Lower container part of a sterile container, said lower container part being closable by an upper container part of the sterile container, said lower container part and said upper container part defining, in a closed position, a container interior, a sealing device being held on said lower container part for gastight or germ-proof sealing of the sterile container in the closed position, said sealing device comprising a circumferential sealing element bearing against the lower container part and adapted to be placed against the upper container part, said sealing element comprising a lower container part sealing section with a lower container part sealing surface region bearing against the lower container part, and an upper container part sealing section with an upper container part sealing surface region adapted to be placed against the upper container part, and said sealing device being of a two-part design, and further comprising, in addition to the sealing element as a first part, a pretensioning device for exerting a pretensioning force on at least the upper container part sealing section in a direction away from the lower container part as a second part, wherein a sealing function of the sealing device is separated into two functions, a pretensioning function performed by the pretensioning device and a bearing function performed by the sealing element.

2. Upper container part of a sterile container, said upper container part being designed to close a lower container part of the sterile container, said upper container part and said lower container part defining, in a closed position, a container interior, a sealing device being held on said upper container part for gastight or germ-proof sealing of the sterile container in the closed position, said sealing device comprising a circumferential sealing element bearing against the upper container part and adapted to be placed against the lower container part, said sealing element comprising an upper container part sealing section with an upper container part sealing surface region bearing against the upper container part, and a lower container part sealing section with a lower container part sealing surface region adapted to be placed against the lower container part, and said sealing device being of a two-part design, and further comprising, in addition to the sealing element as a first part, a pretensioning device for exerting a pretensioning force on at least the lower container part sealing section in a direction away from the upper container part as a second part, wherein a sealing function of the sealing device is separated into two functions, a pretensioning function performed by the pretensioning device and a bearing function performed by the sealing element.

3. Sterile container having a lower container part and an upper container part for closing the lower container part, said lower container part and said upper container part defining, in a closed position, a container interior, a sealing device being provided for gastight or germ-proof sealing of the sterile container in the closed position, said sealing device comprising a circumferential sealing element bearing against both the lower container part and the upper container part in the closed position, said sealing element comprising an upper container part sealing section with an upper container part sealing surface region bearing against the upper container part, and a lower container part sealing section with a lower container part sealing surface region bearing against the lower container part, and said sealing device being of a two-part design, and further comprising, in addition to the sealing element as a first part, a pretensioning device for exerting a pretensioning force on at least the lower container part sealing section in a direction towards the lower container part or on the upper container part sealing section in a direction towards the upper container part as a second part, wherein a sealing function of the sealing device is separated into two functions, a pretensioning function performed by the pretensioning device and a bearing function performed by the sealing element.

4. Sterile container in accordance with claim 3, wherein the pretensioning device is arranged so as to exert the pretensioning force on the lower container part sealing section and on the upper container part sealing section.

5. Sterile container in accordance with claim 3, wherein: (i) the lower container part sealing section and the lower container part are arranged for movement relative to each other, or the upper container part sealing section and the upper container part are arranged for movement relative to each other, or (ii) the lower container part sealing section and the lower container part are arranged for movement relative to each other, and the upper container part sealing section and the upper container part are arranged for movement relative to each other.

6. Sterile container in accordance with claim 3, wherein the lower container part sealing section is firmly connected to the lower container part or the upper container part sealing section is firmly connected to the upper container part.

7. Sterile container in accordance with claim 3, wherein the lower container part sealing section is undetachably connected to the lower container part or the upper container part sealing section is undetachably connected to the upper container part.

8. Sterile container in accordance with claim 3, wherein the sealing element is of an integral configuration.

9. Sterile container in accordance with claim 3, wherein the sealing element is of tube-shaped or pipe-shaped configuration.

10. Sterile container in accordance with claim 3, wherein the sealing element defines a circumferential cavity.

11. Sterile container in accordance with claim 3, wherein the pretensioning device is at least partly covered or surrounded by the sealing element.

12. Sterile container in accordance with claim 3, wherein the sealing element completely encloses the pretensioning device.

13. Sterile container in accordance with claim 3, wherein the pretensioning device comprises at least one pretensioning member, which exerts the pretensioning force on at least the lower container part sealing section in the direction towards the lower container part or on the upper container part sealing section in the direction towards the upper container part.

14. Sterile container in accordance with claim 13, wherein only a single pretensioning member of self-contained configuration is provided.

15. Sterile container in accordance with claim 13, wherein the at least one pretensioning member defines a pretensioning member longitudinal line, and wherein the at least one pretensioning member bears with an outer surface oriented transversely to the pretensioning member longitudinal line, against at least one of the upper container part sealing section and the lower container part sealing section.

16. Sterile container in accordance with claim 13, wherein the at least one pretensioning member defines a pretensioning member longitudinal line, and wherein the at least one pretensioning member exerts a force acting transversely to the pretensioning member longitudinal line on at least one of the upper container part sealing section and the lower container part sealing section.

17. Sterile container in accordance with claim 13, wherein the at least one pretensioning member comprises a helical spring or is configured in the form of a helical spring.

18. Sterile container in accordance with claim 17, wherein the helical spring is of self-contained configuration.

19. Sterile container in accordance with claim 17, wherein the helical spring defines an all-round helical line, and wherein the helical spring exerts a force acting transversely to the helical line on at least one of the upper container part sealing section and the lower container part sealing section.

20. Sterile container in accordance with claim 3, wherein the sealing element is configured in the form of a profiled strand.

21. Sterile container in accordance with claim 3, wherein the sealing element comprises a pretensioning device receptacle for at least partly receiving the pretensioning device.

22. Sterile container in accordance with claim 3, wherein the sealing device is arranged in a circumferential groove on the upper container part or on the lower container part.

23. Sterile container in accordance with claim 3, wherein the pretensioning device is held on the sealing element.

24. Sterile container in accordance with claim 3, wherein the pretensioning device is at least partly made of a metal.

25. Sterile container in accordance with claim 3, wherein the sealing element is made of a plastic material.

* * * * *